(12) United States Patent
Suzuki et al.

(10) Patent No.: US 9,542,768 B2
(45) Date of Patent: Jan. 10, 2017

(54) APPARATUS, METHOD, AND PROGRAM FOR PROCESSING 3D MICROPARTICLE DATA

(71) Applicant: Sony Corporation, Tokyo (JP)

(72) Inventors: Shunsuke Suzuki, Kanagawa (JP); Atsuo Fujimaki, Tokyo (JP); Kenji Shoda, Kanagawa (JP)

(73) Assignee: Sony Corporation, Tokyo (JP)

( * ) Notice: Subject to any disclaimer, the term of this patent is extended or adjusted under 35 U.S.C. 154(b) by 0 days.

(21) Appl. No.: 14/838,780

(22) Filed: Aug. 28, 2015

(65) Prior Publication Data

US 2015/0371427 A1 Dec. 24, 2015

Related U.S. Application Data

(63) Continuation of application No. 13/885,637, filed as application No. PCT/JP2011/077195 on Nov. 25, 2011, now abandoned.

(30) Foreign Application Priority Data

Dec. 3, 2010 (JP) .................... 2010-269944

(51) Int. Cl.
*G06T 15/00* (2011.01)
*G06T 11/20* (2006.01)
(Continued)

(52) U.S. Cl.
CPC ............... *G06T 15/00* (2013.01); *G01N 15/14* (2013.01); *G06T 3/40* (2013.01); *G06T 3/60* (2013.01);
(Continued)

(58) Field of Classification Search
CPC ............ G01N 15/14; G01N 2015/1006; G01N 2015/1477; G01N 2015/1402; G06T 2210/56; G06T 3/60; H04N 13/0275
See application file for complete search history.

(56) References Cited

U.S. PATENT DOCUMENTS

| | | | |
|---|---|---|---|
| 5,423,321 | A | 6/1995 | Fontenot |
| 5,428,715 | A | 6/1995 | Suzuki |

(Continued)

FOREIGN PATENT DOCUMENTS

| | | |
|---|---|---|
| JP | 10-124702 | 5/1998 |
| JP | 10-318904 | 12/1998 |

(Continued)

OTHER PUBLICATIONS

International Search Report issued in connection with International Patent Application PCT/JP2011/077195, dated Dec. 27, 2011.

(Continued)

*Primary Examiner* — Jacinta M Crawford
*Assistant Examiner* — Jonathan M Cofino
(74) *Attorney, Agent, or Firm* — K&L Gates LLP

(57) ABSTRACT

An information processing apparatus for 3D microparticle data analysis is provided. The information processing apparatus includes a data storage unit configured to store measurement data of microparticles; a data processing unit configured to create a 3D image in a coordinate space with three types of variables from the measurement data, the 3D image represents a characteristic distribution of the microparticles; and a display unit configured to display the 3D image, wherein in a case that a gating region is set in the 3D image, the 3D image is rotated or scaled up or down along with the gating region on the display unit. An information processing method and program for 3D microparticle data analysis are also provided.

17 Claims, 10 Drawing Sheets

(51) Int. Cl.
    *G01N 15/14*     (2006.01)
    *G06T 3/40*     (2006.01)
    *G06T 3/60*     (2006.01)
    *H04N 13/02*     (2006.01)
    *H04N 13/04*     (2006.01)
    *G01N 15/10*     (2006.01)

(52) U.S. Cl.
    CPC ......... *G06T 11/206* (2013.01); *H04N 13/0203* (2013.01); *H04N 13/0275* (2013.01); *H04N 13/0282* (2013.01); *H04N 13/0409* (2013.01); *H04N 13/0436* (2013.01); *H04N 13/0447* (2013.01); *G01N 2015/1006* (2013.01); *G01N 2015/1477* (2013.01); *G06T 2200/04* (2013.01); *G06T 2200/08* (2013.01); *G06T 2210/56* (2013.01)

(56) References Cited

U.S. PATENT DOCUMENTS

| | | | |
|---|---|---|---|
| 5,598,164 | A | 1/1997 | Reppas et al. |
| 5,776,709 | A * | 7/1998 | Jackson ............. G01N 33/5094 356/336 |
| 6,243,488 | B1 | 6/2001 | Penna |
| 6,629,065 | B1 | 9/2003 | Gadh et al. |
| 6,690,371 | B1 * | 2/2004 | Okerlund ............. G06T 11/008 345/424 |
| 7,764,282 | B2 | 7/2010 | Chiba |
| 2005/0135670 | A1 * | 6/2005 | Vaidyanathan ....... G06T 7/0057 382/154 |
| 2006/0221325 | A1 * | 10/2006 | Wells ................. G01N 15/1404 356/73 |
| 2007/0098299 | A1 * | 5/2007 | Matsumoto ............. G06T 15/08 382/284 |
| 2009/0028442 | A1 * | 1/2009 | Kimmel ............. G06K 9/00214 382/218 |
| 2010/0110103 | A1 * | 5/2010 | Ramirez ................. G06K 9/622 345/619 |
| 2011/0109617 | A1 | 5/2011 | Snook et al. | |

FOREIGN PATENT DOCUMENTS

| | | |
|---|---|---|
| JP | 2000-156875 | 6/2000 |
| JP | 2000-268198 | 9/2000 |
| JP | 2010-033528 A | 2/2010 |

OTHER PUBLICATIONS

Herzenberg et al., "Interpreting flow cytometry data: a guide for the perplexed," Jul. 2006, Nature Immunology, vol. 7, No. 7, pp. 681-685.

Weiskopf et al., "A Depth-Cueing Scheme Based on Linear Transformations in Tristimulus Space," Sep. 2002, Visualisierung und Interaktive Systeme, No. 8, pp. 1-11.

Lee et al., "Line drawings via abstracted shading," Jul. 2007, ACM Transactions on Graphics, vol. 26, No. 3, Article 18, pp. 1-5.

Japanese Office Action issued October 15, 2015, for corresponding Japanese Appln. No. 2012-546830 (5 pages).

Japanese Office Action issued on May 26, 2016 in corresponding Japanese application No. 2012-546830 (4 pages).

* cited by examiner (A)

(B)

APPARATUS, METHOD, AND PROGRAM FOR PROCESSING 3D MICROPARTICLE DATA

CROSS REFERENCES TO RELATED APPLICATIONS

The present application is a continuation of U.S. patent application Ser. No. 13/885,637 filed on May 15, 2013, which was a national stage of International Patent Application No. PCT/JP2011/077195 filed on Nov. 25, 2011, which claims priority to Japanese Priority Patent Application JP 2010-269944 filed in the Japan Patent Office on Dec. 3, 2010, the entire content of which is hereby incorporated by reference.

BACKGROUND

The present invention relates to a 3D data analysis apparatus, a 3D data analysis method, and a 3D data analysis program. More specifically, the present invention relates to a 3D data analysis apparatus and the like for displaying measurement data of microparticles with a 3D stereoscopic image.

To analyze microparticles including biologically relevant particles such as cells, microbes, and liposomes and synthetic particles such as latex particles, gel particles, and particles for industrial use, a microparticle measurement apparatus is used which introduces a dispersion liquid of microparticles in a flow channel and measures the microparticles optically, electrically, or magnetically.

As an example, there is a particle analyzer that distinguishes synthetic particles on the basis of sizes or shapes. Examples of a parameter (variable) which can be measured by the particle analyzer include an elemental composition and a particle diameter of a microparticle.

Further, to analyze biologically relevant particles, a flow cytometer (flow cytometry) is used. Examples of a parameter which can be measured by the flow cytometer include forward scattered light (FS), side scatter (SS), fluorescent light (FL), and impedance of microparticles. The forward scattered light (FS), the side scatter (SS), and the fluorescent light (FL) are used as parameters that indicate an optical characteristic of a cell or a microbe (hereinafter, simply referred to as "cell"), and the impedance is used as a parameter that indicates an electrical characteristic of a cell.

Specifically, first, the forward scattered light is light that is scattered at a small angle in a forward direction with respect to an axis of laser light and includes scattered light, diffracted light, and refracted light of laser light which is generated on a surface of a cell. The forward scattered light is mainly used as a parameter that indicates the size of a cell. Next, the side scatter is light that is scattered at approximately 90 degrees with respect to an axis of laser light and is scattered light of laser light that is generated in a granule or a core inside a cell. The side scatter is mainly used as a parameter that indicates an internal structure of a cell. Further, the fluorescent light is light that is generated from a fluorochrome labeled to a cell and is used as a parameter that indicates existence or nonexistence of a cell surface antigen recognized by a fluorochrome-labeled antibody, the amount of a nucleic acid to which a fluorochrome is combined, or the like. Furthermore, the impedance is measured by an electrical resistance method and used as a parameter that indicates a cell volume.

To analyze measurement data in a flow cytometer, a data analysis apparatus is used in which measurement values of cells are plotted with these measurement parameters being as axes, thereby creating a diagram that shows a characteristic distribution of the cells in a cell population. A one-dimensional distribution chart with the use of one measurement parameter is called as a histogram, which is created with an X axis indicating the measurement parameter, and a Y axis indicating the number of cells (count). Further, a two-dimensional distribution chart in which two measurement parameters are used is called as a cytogram, which is created by plotting cells on the basis of the measurement values in a coordinate plane with the X axis indicating one measurement parameter and the Y axis indicating the other measurement parameter.

The cell population as a sample includes unnecessary cells not to be analyzed, so the analysis of the measurement data is performed after a cell small population to be analyzed is selected from the cell population as the sample. The cell small population to be analyzed is selected by specifying an area in which the cell small population exists on the histogram or the cytogram. This operation is called as "gating" because cells as targets are enclosed in an area specified on the histogram or the cytogram.

On the histogram with one measurement parameter as an axis or on the cytogram with one combined measurement parameter as axes, the cell small population to be analyzed and unnecessary cells may exist in an overlapped area in some cases. For example, when a lymphocyte is analyzed with human peripheral blood as a sample, on a cytogram with a forward scattered light (FS) and a side scatter (SS) used for axes, a part of monocyte exists in the same area as the lymphocyte in some cases. Therefore, when performing gating, a user has to specify an area in which only lymphocyte exists so as not to enclose the monocyte.

In order to specify an area so that only a cell small population to be analyzed is enclosed without enclosing unnecessary cells, conventionally, a user has to perform gating while referring to a plurality of histograms or cytograms. Along with improvement of the performance of a flow cytometer, the number of parameters that can be measured is increased, so the user has to refer to more histograms or cytograms. Further, at this time, the user is requested to perform a gating operation while imaging a three-dimensional distribution chart (3D distribution chart) in which two cytograms are combined.

To assist the user in performing the gating operation, Patent Document 1 proposes "an analysis apparatus including a measurement data obtaining means for obtaining first, second, and third measurement data items from an analyte, a 3D distribution chart creating means for creating a 3D distribution chart that indicates a distribution of formed elements contained in the analyte with the first, second, and third measurement data items as axes, an area setting means for variably setting a separate area on the 3D distribution chart, and a reference distribution chart creating means for creating, with respect to formed elements that belongs to the separate area set by the area setting means, at least one of a 2D distribution chart with the first and second measurement data items used as the axes and a frequency distribution chart with the first measurement data item used as the axis" (see, claim 9 of Patent Document 1). By the analysis apparatus, it is possible to set the separate area on the 3D distribution chart while referring to the 2D distribution chart (cytogram) and the frequency distribution chart (histogram) displayed along with the 3D distribution chart. It should be noted that the 3D distribution chart of the analysis apparatus is not viewed stereoscopically but is displayed two-dimensionally on a display.

In relation to the present invention, twin-lens stereo image technology (3D stereoscopic image technology) will be described. In the twin-lens stereo image, first, two images when an object is viewed with a right eye and a left eye are prepared. Then, these images are displayed at the same time, and an image for the right eye is presented only to the right eye, and an image for the left eye is presented only to the left eye. As a result, an image that appears in the eyes at a time when the object is viewed in a 3D space is reproduced, and a user is caused to stereoscopically view the object.

For a 3D display which allows a stereoscopic view, a (a) glasses type, a (b) glasses-free type, and a (c) viewer type are mainly adopted. The (a) glasses type includes an anaglyph type, a polarization filter type, and a time-sharing type. Further, the (b) glasses-free type includes a parallax barrier type and a lenticular type, and the (c) viewer type includes a stereoscope type and a head mount type.

SUMMARY

Problem to be Solved by the Invention

As described above, conventionally, in the data analysis apparatus used for the flow cytometer, at the time of gating, it is necessary for a user to specify the position of a cell small population to be analyzed on a distribution chart while referring to a large number of histograms or cytograms or imaging a three-dimensional distribution chart obtained by combining two cytograms (3D distribution chart).

In view of the above, it is an object of the present invention to provide a data analysis apparatus capable of easily and instinctively specifying microparticles and microparticle small populations to be analyzed on a distribution chart without referring to a large number of histograms or cytograms or imaging a 3D distribution chart.

Means for Solving the Problem

To solve the above-mentioned problem, the present invention provides a 3D data analysis apparatus including a data storage unit to store measurement data of microparticles, an input unit to select three kinds of variables independent of the measurement data, a data processing unit to calculate positions and graphics in a coordinate space with the three kinds of variables being coordinate axes and create a 3D stereoscopic image that represents a characteristic distribution of the microparticles, and a display unit to display the 3D stereoscopic image.

By the 3D data analysis apparatus, it is possible to analyze the measurement data while stereoscopically viewing the 3D distribution chart with the arbitrarily selected three kinds of parameters being the coordinate axes.

Further, the present invention also provides a 3D data analysis method including the steps of selecting three kinds of variables independent of measurement data of microparticles, calculating positions and graphics in a coordinate space with the three kinds of variables being coordinate axes and creating a 3D stereoscopic image that represents a characteristic distribution of the microparticles, and displaying the 3D stereoscopic image. Furthermore, the resent invention also provides a 3D data analysis program causing a computer to execute the steps of calculating positions and graphics in a coordinate space with three kinds of independent variables selected from measurement data of microparticles being coordinate axes and creating a 3D stereoscopic image that represents a characteristic distribution of the microparticles, and displaying the 3D stereoscopic image.

In the present invention, the "microparticles" widely include biologically relevant particles such as cells, microbes, and liposomes, synthetic particles such as latex particles, gel particles, and particles for industrial use, and the like.

The cells include animal cells (hematopoietic cells or the like) and plant cells. The microbes include bacteria such as coli bacilli, viruses such as tobacco mosaic viruses, and fungi such as yeast. The biologically relevant particles include chromosomes, liposomes, mitochondrion, organelle (cell organelle), and the like that form various cells. Further, the biologically relevant particles can include biologically relevant polymer such as nucleic acids, proteins, and complexes of these. The particles for industrial use may be organic or inorganic polymeric materials, metal, or the like. The organic polymeric materials include polystyrene, styrene-divinylbenzene, polymethyl methacrylate, and the like. The inorganic polymeric materials include glass, silica, magnetic materials, and the like. The metal include gold colloid, aluminum, and the like. These microparticles generally have spherical forms but may be non-spherical forms. Further, the sizes, masses, and the like of these microparticles are also not limited particularly.

Effect of the Invention

According to the present invention, the data analysis apparatus is provided which is capable of easily and instinctively specifying microparticles and microparticle small populations to be analyzed without referring to a large number of histograms or cytograms or imaging a 3D distribution chart.

Additional features and advantages are described herein, and will be apparent from the following Detailed Description and the figures.

DETAILED DESCRIPTION

Hereinafter, preferred embodiments for carrying out the present invention will be described with reference to the drawings. It should be noted that the embodiments to be described below are an example of a representative embodiment of the present invention, so the scope of the present invention is not interpreted narrowly because of the embodiments. It should be noted that the description will be given in the following order.

Figure 1:
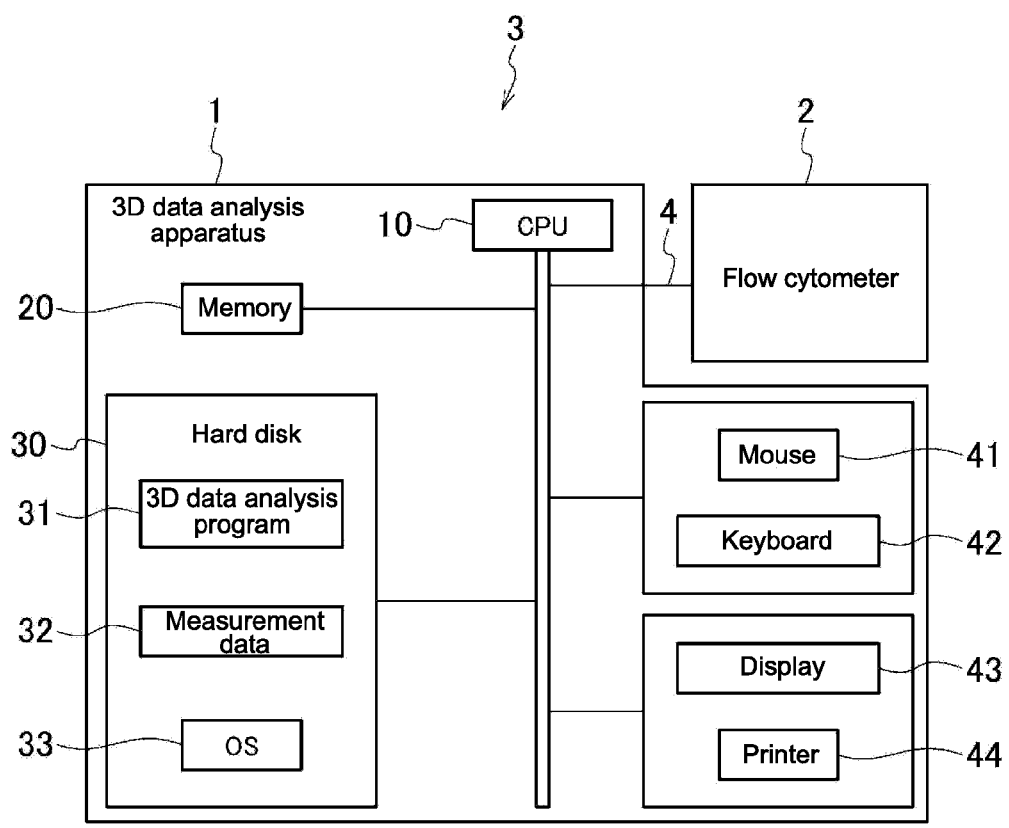
FIG. 1 is a block diagram for explaining the structure of a 3D analysis apparatus according to the present invention, which is provided contiguously with a flow cytometer.
Figure 2:
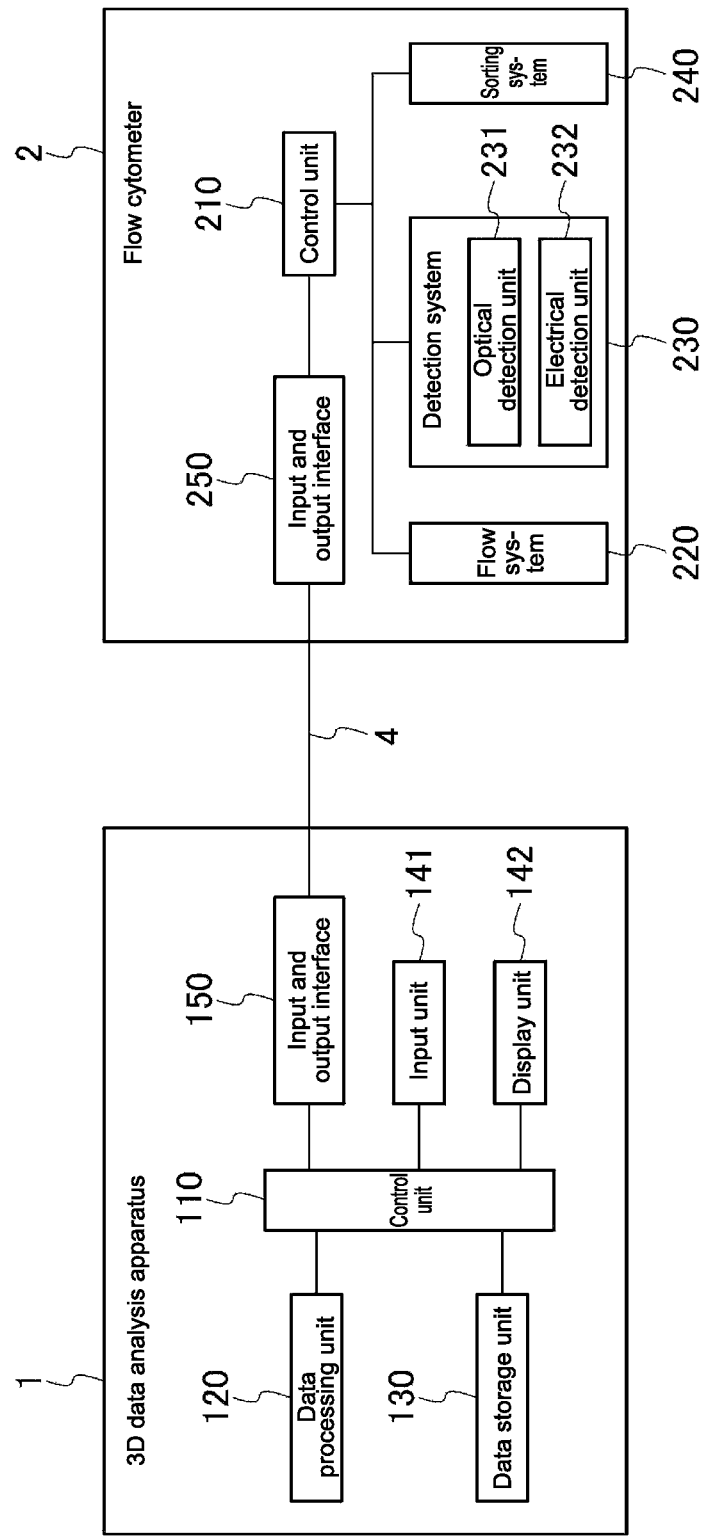
FIG. 2 is a block diagram for explaining the functional structure of the 3D analysis apparatus according to the present invention.

1. Structure of 3D data analysis apparatus
2. Display of 3D stereoscopic image
3. Characteristics of 3D stereoscopic image
   (3-1) shape of graphic
   (3-2) shade process for graphic
   (3-3) coordinate axis
   (3-4) moving image
4. 3D data analysis program
1. Structure of 3D Data Analysis Apparatus FIG. 1 shows the structure of a 3D data analysis apparatus according to the present invention. Here, shown is an embodiment in which the 3D data analysis apparatus is provided contiguously with a microparticle measurement apparatus, thereby constituting a microparticle analysis system. Further, FIG. 2 shows the functional structure of the microparticle analysis system. Hereinafter, an example in which a flow cytometer is used as the microparticle measurement apparatus will be described.

The 3D data analysis apparatus denoted by reference numeral 1 in the figure constitutes a microparticle analysis system 3 by being connected to a flow cytometer 2 with a communication cable 4. The 3D data analysis apparatus 1 includes a central processing unit (CPU) 10, a memory 20, a hard disk 30, a user interface, and the like. In the hard disk 30, a 3D data analysis program 31, measurement data 32 of microparticles, an operating system (OS) 33, and the like are stored and held. The user interface includes a mouse 41, a keyboard 42, and the like which receive an input of information from a user and a display 43, a printer 44, and the like which output information to the user. It should be noted that an input device such as a stick controller and a pen tablet may be provided, instead of the mouse 41 and the keyboard 42 or along with these devices.

A data storage unit 130 (hard disk 30) stores the measurement data 32 of the microparticles (cells) which is output from the flow cytometer 2. The measurement data output from an input and output interface 250 of the flow cytometer 2 is input to an input and output interface 150 of the 3D data analysis apparatus 1 through the communication cable 4 and stored in a data storage unit 30 (hard disk 30).

The measurement data 32 is processed in a data processing unit 120. The data processing unit 120 starts the processing upon reception of an input from an input unit 141 (mouse 41, keyboard 42, or the like) by a user. That is, when the user selects and inputs three kinds of variables (parameters) independent of the measurement data 32, the data processing unit 120 creates a 3D distribution chart that represents a characteristic distribution of microparticles with the parameters selected being as the coordinate axes. The 3D distribution chart is created by plotting the microparticles in the coordinate space with the parameters selected being as the coordinate axes. The plotting of the microparticles are performed by calculating positions and a graphic in the coordinate space of the microparticles from measurement values of the parameters selected and drawing the graphic calculated on the position calculated.

Here, the "parameters independent" refer to parameters which are selected from the forward scattered light (FS), the side scatter (SS), the fluorescent light (FL), the impedance, and the like of the microparticles and are different from each other. The fluorescent light (FL) can be dealt as a parameter different for each wavelength of fluorochrome labeled to the microparticles and represented by FL1, FL2 to FLn (n: 3 or more integer), or the like. As the three kinds of parameters independent, a combination of the forward scattered light (FS), the side scatter (SS), and the fluorescent light (FL1) or a combination of the forward scattered light (FS), the side scatter (SS), and the impedance are given as examples. In addition, the three kinds of parameters independent can be a combination arbitrarily selected from the measurement data.

The 3D distribution chart created by the data processing unit 120 is displayed as a 3D stereoscopic image on a display unit 142 (display 43). One or two or more 3D stereoscopic images can be displayed on the display unit 142. In the case where the two or more 3D stereoscopic images are displayed, 3D stereoscopic images obtained by observing the same 3D distribution chart in a plurality of different directions may be displayed, or 3D stereoscopic images of a plurality of 3D distribution charts may be displayed with at least one of three kinds of parameters selected being different. The 3D stereoscopic images are twin-lens stereo images to be described in detail in the following.

Further, in the case where the measurement data 32 includes measurement values at a plurality of different time points, the display unit 142 may display a 3D distribution chart that represents a characteristic distribution of microparticles at the plurality of time points with a 3D stereoscopic image. Examples of the measurement data that includes measurement values at a plurality of time points include data obtained by measuring association or dissociation of cell-surface molecular complexes with time with the use of the fluorescence resonance energy transfer (FRET), data obtained by measuring a change of a cell membrane with time with the use of fluorochrome the fluorescence wavelength of which varies depending on a charge of the cell membrane, data obtained by measuring the intensity of expression of a cell-surface molecule by being correlated with an inflow response of intracellular calcium, and the like.

The 3D stereoscopic images of the 3D distribution chart at the plurality of time points may be displayed in a row at the same time or may be switched and displayed one by one. In the case where the switching display of the 3D stereoscopic display is performed, the switching may be automatically performed or may be performed on the basis of an input signal of a user. By displaying the 3D stereoscopic images of the 3D distribution chart at the plurality of time points, it is possible for a user to analyze the data while confirming a change with time in the characteristic distribution of the microparticles, and a multifactorial analysis can be performed as compared to the case where time (temporal axis) is added to three kinds of parameters (coordinate axes).

The display of the 3D stereoscopic image on the display unit 142 may be performed by arbitrarily rotating or scaling up or down on the basis of an input signal of a user from the input unit 141 (mouse 41, keyboard 42, or the like). Further, in the case where a separate area for gating is set in a coordinate space of the 3D distribution chart on the basis of the input signal from the input unit 141, the 3D stereoscopic image is rotated or scaled up or down along with a 3D shape that represents the separate area displayed in the 3D stereoscopic image.

The flow cytometer 2 can have the same structure as the conventionally known apparatus or can be configured by appropriately modifying this, specifically, is constituted of a control unit 210, a flow system 220, a detection system 230, an input and output interface 250, and the like.

In a flow channel formed in a flow cell or micro chip, the flow system 200 causes a laminar flow of a sample liquid containing the microparticles to flow to the center of a laminar flow of a sheath liquid to arrange the microparticles in the laminar flow in a row. The detection system 230 obtains a parameter value that indicates the characteristic of the microparticles that are flown through the flow channel. Specifically, an optical detection unit 231 irradiates the microparticles flown with light, detects scattered light, fluorescent light, or the like generated from the microparticles, and obtains the intensity thereof. The optical detection unit 231 includes a laser light source, lens, a mirror, a filter, an area image pickup element such as a CCD and a CMOS element, a PMT (photo multiplier tube), or the like. Further, an electrical detection unit 232 includes an electrode provided so as to be opposed to the microparticles flown, and obtains an impedance, a capacitance value, an inductance, and the like of the microparticles. The flow cytometer 2 may be provided with a sorting system 240 for sorting the microparticles which are determined to have a desired characteristic as a result of the analysis. For the sorting system 240, for example, it is possible to adopt a system of ejecting a droplet containing the microparticles to a space outside the flow cell and controlling a moving direction of the droplet, thereby collecting only desired microparticles into a container.

The measurement values of the intensities of the scattered light, the fluorescent light, and the like detected in the detection system 230 or the measurement values of the impedance, the capacitance value, the inductance, and the like are converted into electrical signals and output from the input and output interface 250 as the measurement data.

2. Display of 3D Stereoscopic Image

Figure 3:
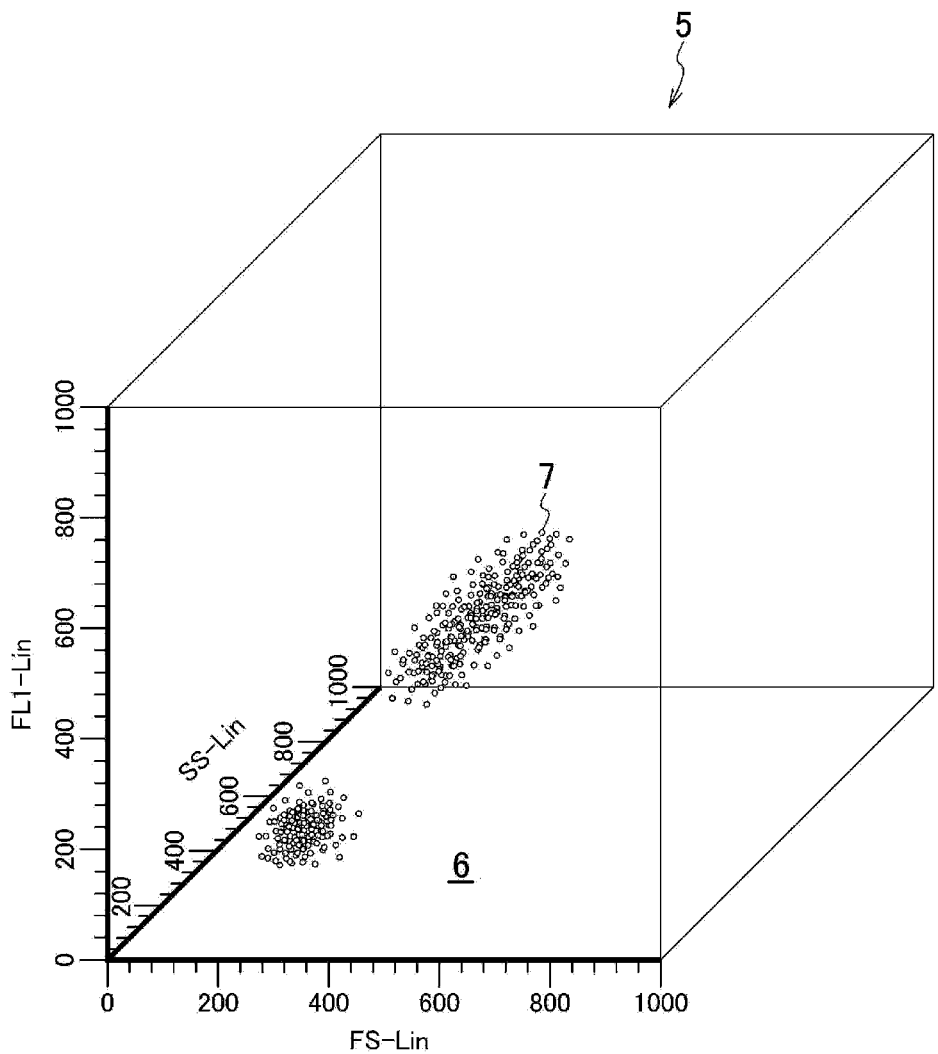
FIG. 3 is a schematic diagram for explaining a 3D distribution chart displayed by the 3D data analysis apparatus according to the present invention.

FIG. 3 schematically shows a 3D distribution chart displayed by the 3D data analysis apparatus according to the present invention. The 3D distribution chart is displayed as a 3D stereoscopic image on the display unit 142 and can be stereoscopically visually confirmed by a user.

A 3D distribution chart 5 shows a characteristic distribution of the microparticles in a coordinate space 6 with the three kinds of parameters selected by a user being as the coordinate axes. In the 3D distribution chart 5, at positions calculated from the measurement values of the parameters selected, graphics 7 corresponding to the respective microparticles are drawn.

In the figure, the case where the three kinds of parameters are a combination of the forward scattered light (FS-Lin: X axis), the side scatter (SS-Lin: Y axis), and a first fluorescent light (FL1-Lin: Z axis) is given as an example. The parameters used for the respective coordinate axes can be a combination selected arbitrarily. For example, the first fluorescent light (FL1), a second fluorescent light (FL2), and an impedance can be used for the X axis, the Y axis, and the Z axis, respectively.

Figure 4:
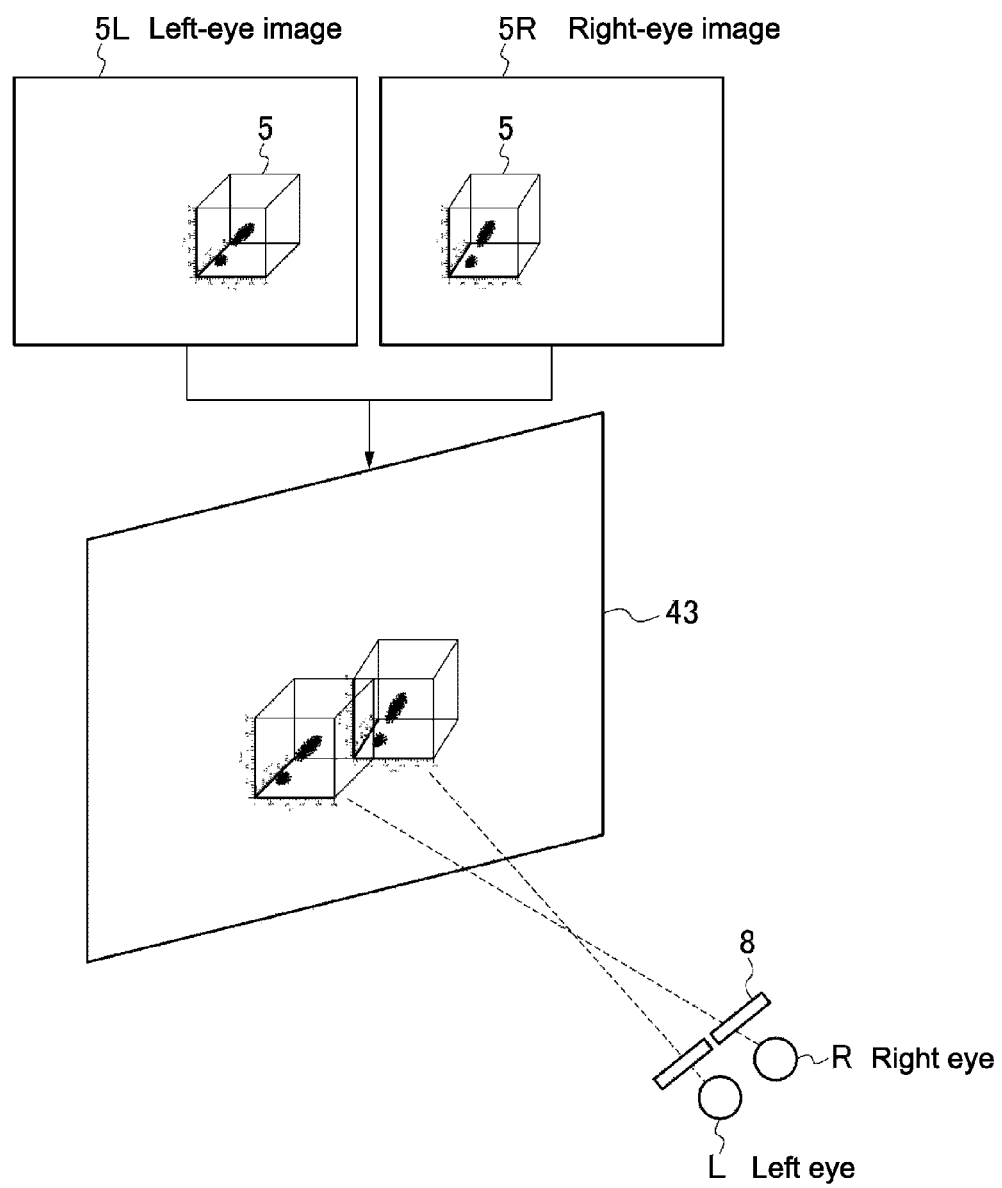
FIG. 4 is a schematic diagram for explaining a twin-lens stereo image (3D stereoscopic image) displayed by the 3D data analysis apparatus according to the present invention.

The 3D stereoscopic display of the 3D distribution chart is performed with a twin-lens stereo image. FIG. 4 schematically shows a twin-lens stereo image displayed by the 3D data analysis apparatus according to the present invention.

When a user selects the parameters, the data processing unit 120 creates the 3D distribution chart 5 and creates an image at a time when the distribution chart is viewed with the left eye (left-eye image 5L) and an image when viewed with the right eye (right-eye image 5R). The display unit 142 (display 43) displays the left-eye image 5L and the right-eye image 5R at the same time, and separate presentation is performed so that the left-eye image 5L is presented only to the left eye, and the right-eye image 5R presented only to the right eye.

For example, in a time-division system, which is one of the glasses type, the separation presentation can be performed by alternately displaying the left-eye image 5L and the right-eye image 5R with a minute time difference and causing shutter glasses 8 to be synthesized with this. In addition, for the separation distribution, another glasses type such as an anaglyph type and a polarization filter type, the glasses-free type such as a parallax barrier type and a lenticular type, and the viewer type such as a stereoscope type and a head mount type may be used.

By performing the separation presentation of the left-eye image 5L and the right-eye image 5R, the display 43 reproduces an image seen in the eyes at the time when the 3D distribution chart is viewed in the 3D space and causes a user to stereoscopically view the distribution chart.

As described above, in the 3D data analysis apparatus 1, it is possible for a user to analyze the measurement data while stereoscopically viewing the 3D distribution chart with the arbitrarily selected three kinds of parameters being as the coordinate axes. Therefore, in the 3D data analysis apparatus 1, it is possible to easily and instinctively specify the microparticles and microparticle small populations to be analyzed on the distribution chart, so it is unnecessary to refer to a lot of histograms or cytograms or imaging the 3D distribution chart as in the conventional way. In addition, the parameters used for the coordinate axes are arbitrarily combined to display the 3D distribution chart, with the result that it is possible to obtain information relating to the three characteristics of the microparticles with one graph. Further, by displaying the 3D stereoscopic image obtained by observing the same 3D distribution chart in a plurality of different directions or displaying the 3D stereoscopic images of a plurality of 3D distribution charts with at least one of three kinds of parameters selected being different, it is possible to obtain more pieces of information. Thus, in the 3D analysis apparatus 1, it is possible to perform an efficient analysis by reducing the number of graphs to be referred to as compared to the display with conventional histograms or cytograms.

3. Characteristics of 3D Stereoscopic Image

Hereinafter, the characteristics of the 3D stereoscopic image displayed by the 3D data analysis apparatus according to the present invention will be described in order.

(3-1) Shape of Graphic

The graphics corresponding to the microparticles, which are each denoted by the reference numeral 7 in FIG. 3, are calculated as polyhedrons constituted of polygons each having a predetermined shape and displayed in the 3D stereoscopic image. As described above, on the basis of the measurement values of the parameters selected by a user, the data processing unit 120 calculates the positions and the graphics 7 of the microparticles in the coordinate space and creates the 3D distribution chart. At this time, by calculating the graphic 7 as the polyhedron constituted of the polygons having the predetermined shape, it is possible to reduce a calculation load in the data processing unit 120. Further, by displaying, in the 3D stereoscopic image, the graphic 7 as the polyhedron constituted of the polygons having the predetermined shape, it is possible to increase the stereoscopic effect of an image when the image is stereoscopically viewed.

Figure 5:
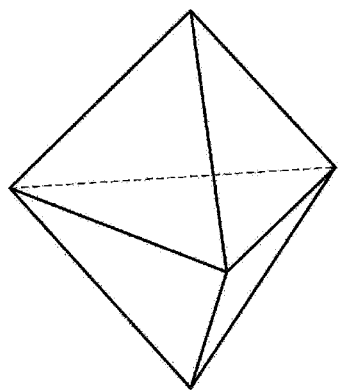
FIG. 5 is a schematic diagram for explaining shapes of graphics corresponding microparticles in the 3D stereoscopic image.
Figure 5:
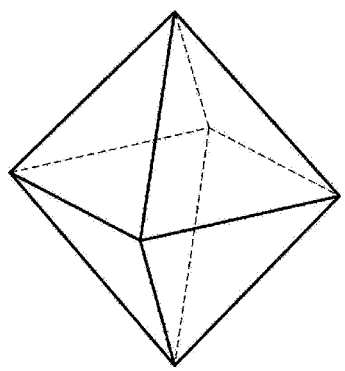

As the polyhedron constituted of the polygons having the predetermined shape, for example, a hexahedron constituted of six triangular polygons as shown in (A) of FIG. 5 or an octahedron constituted of eight polygons as shown in (B) of FIG. 5 can be employed. The shapes of the graphic 7 are not particularly limited as long as a polyhedron constituted of polygons each having a predetermined shape is provided. In a viewpoint of the stereoscopic effect and the reduction of the calculation load, the hexahedron or the octahedron is preferable.

(3-2) Shade Process for Graphic

In the 3D stereoscopic image, the graphics 7 observed forward when stereoscopically viewed are indicated with increased shading, and the graphics 7 observed backward are indicated with decreased shading. In this way, a process of changing the shading of the graphics 7 is referred to as a "shade process" hereinafter.

Figure 6:
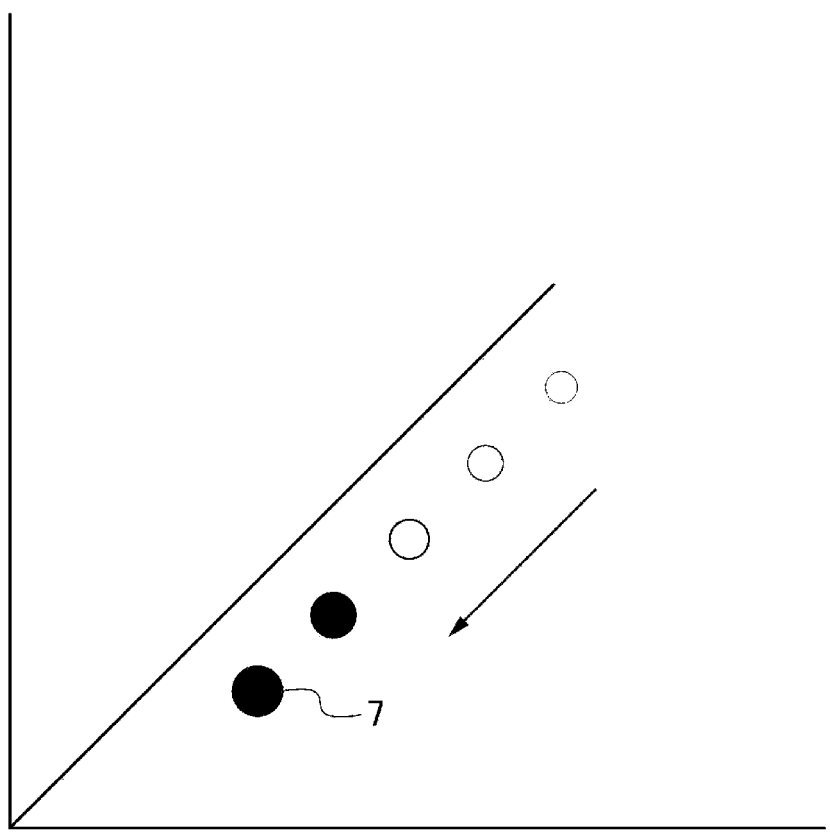
FIG. 6 is a conceptual diagram for explaining a stereoscopic observation image of a graphic which is subjected to a shade process.

A conceptual diagram of a stereoscopic observation image (hereinafter, simply referred to as "stereoscopic image") of the graphic 7 which has been subjected to the shade process is shown in FIG. 6. Toward a direction of the arrow in the figure, the graphics 7 observed forward are darker, and the graphics 7 observed backward are lighter. In this way, by performing the shade process for the graphics 7, a depth is given to the stereoscopic image of the 3D stereoscopic image, and the stereoscopic effect can be increased.

Figure 7:
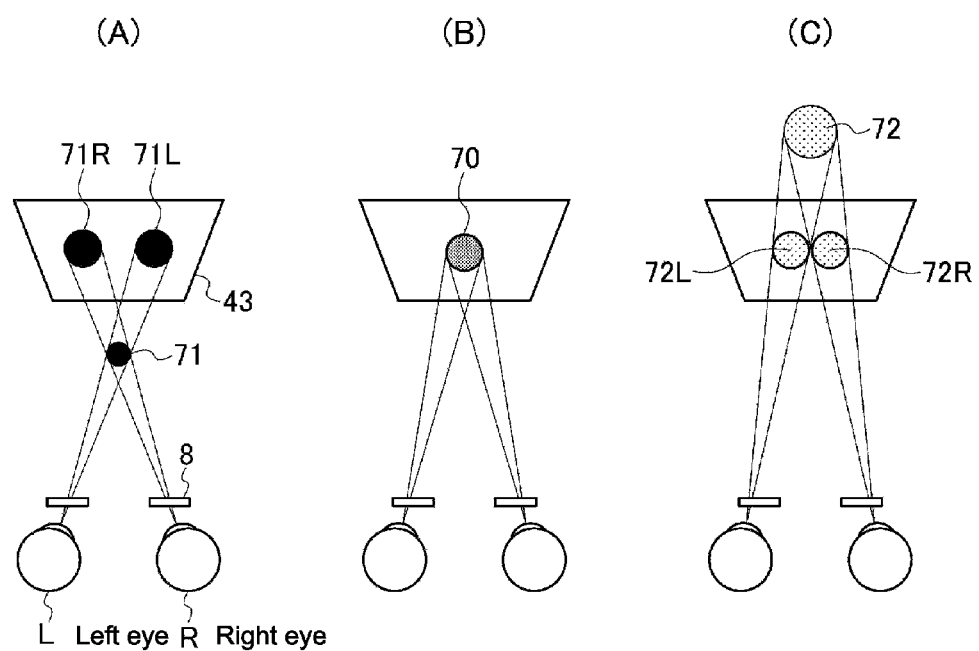
FIG. 7 is a schematic diagram for explaining a method of processing the shade process.

With reference to FIG. 7, the method of shade process will be described. On the display 43, a left-eye image and a right-eye image are displayed at the same time, and the left-eye image and the right-eye image of a graphic 70 observed at a position on a screen of the display 43 when stereoscopically viewed are displayed in a superimposed manner (see, (B) of FIG. 7).

In the case where the left-eye image displayed on the display 43 is positioned rightward as compared to the right-eye image (see, (A) of FIG. 7), the graphic is stereoscopically viewed forward as compared to the position on the screen of the display 43. The stereoscopic image of the graphic observed in a pop-up manner from the screen position is denoted by the reference numeral 71 in the figure, and the left-eye image and the right-eye image of the graphic 71 displayed on the display 43 are denoted by the symbols 71L and 71R, respectively. On the other hand, in the case where the left-eye image displayed on the display 43 is positioned leftward as compared to the right-eye image (see, (C) of FIG. 7), the graphic is stereoscopically viewed backward from the position on the screen of the display 43. The stereoscopic image of the graphic observed in a pop-up manner from the screen position is denoted by the reference numeral 72, and the left-eye image and the right-eye image of the graphic 71 displayed on the display 43 are denoted by the symbols 72L and 72R, respectively.

In the shade process, the left-eye image 71L and the right-eye image 71R of the graphic 71 observed forward are displayed to be darker, and the left-eye image 72L and the right-eye image 72R of the graphic 72 observed backward are displayed to be lighter.

(3-3) Coordinate Axes

Figure 8:
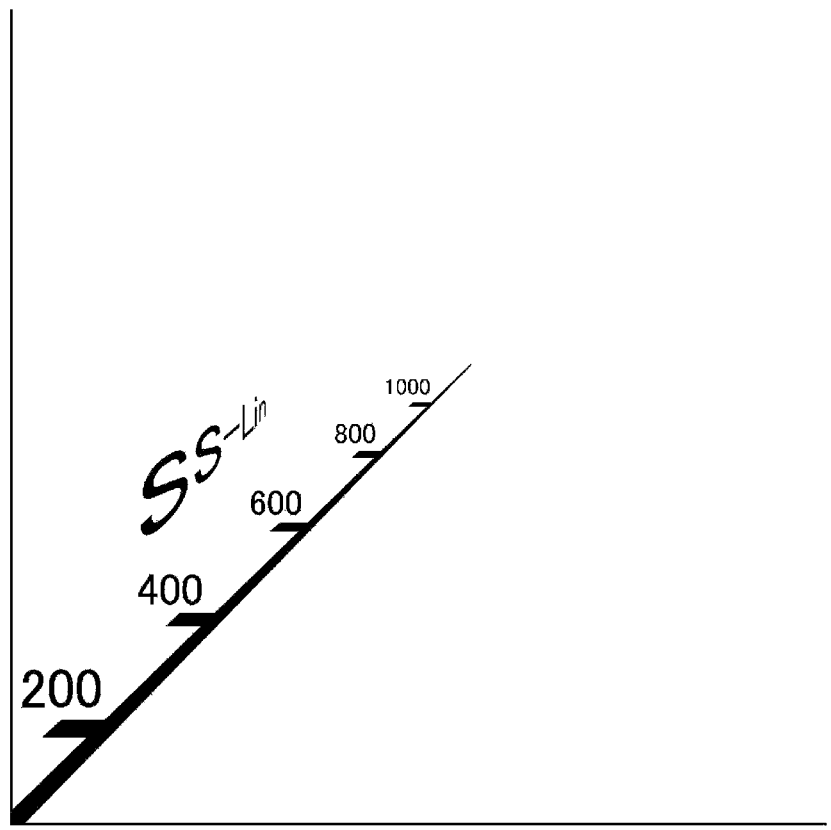
FIG. 8 is a conceptual diagram for explaining a stereoscopic observation image of coordinate axes.

In the 3D stereoscopic image, the coordinate axis is displayed to be thicker as a part observed forward when the stereoscopic viewing is performed, and the coordinate axis is displayed to be thinner as a part observed backward. A conceptual diagram of a stereoscopic image of the coordinate axis having a varied thickness is shown in FIG. 8. In this way, by changing the thickness of the coordinate axis, it is possible to increase the stereoscopic effect by giving a depth to the stereoscopic image of the 3D stereoscopic image.

Further, as shown in FIG. 8, scale intervals of the coordinate axis are set to be wider as a part observed forward when the stereoscopic viewing is performed, and the scale intervals thereof are set to be narrower as a part observed backward, with the result that a further depth can be given to the stereoscopic image. Furthermore, the name of the coordinate axis (SS-Lin in the figure) and the characters of the scale values (200, 400, 600, 800, 1000, in the figure) are displayed to be larger toward the front and displayed to be smaller toward the back, with the result that the same effect is obtained. It should be noted that the process of changing the thickness of the coordinate axis, the size of the scale intervals, and the size of the characters can also be performed through an application of the shade process described above.

The coordinate axes may be a biexponential axis having characteristics of a linear axis and a logarithmic axis in combination. The detail of the biexponential axis is described in "A New "Logicle" Display Method Avoids Deceptive Effects of Logarithmic Scaling for Low Signals and Compensated Data. Cytometry part A 69A: 541-551, 2006", for example.

In the biexponential axis, with respect to such data that a measurement value of a parameter selected as a coordinate axis is smaller than a predetermined value, a function the main function element of which is a linear function is applied, thereby obtaining the positions of the graphics 7 corresponding to the microparticles. Further, with respect to such data that a measurement value is larger than the predetermined value, a function the main function element of which is a logarithmic function is applied, thereby obtaining the positions of the graphics 7. More simply, the biexponential axis can be set so that an area larger than the predetermined area is a logarithmic axis, and an area smaller than the predetermined area is a linear axis. By using the biexponential axis for the coordinate axes of the 3D distribution chart, it is possible to perform displaying at a wider dynamic range for which the characteristics of the logarithmic axis are used, and at the same time, to perform displaying with negative numbers because of the characteristics of the linear axis. It should be noted that at least one of the coordinate axes of the 3D distribution chart may be a biexponential axis.

(3-4) Moving Image

As described above, the display of the 3D stereoscopic image to the display unit 142 (display 43) may be performed by arbitrarily rotating or scaling up or down on the basis of an input signal of the user from the input unit 141 (mouse 41, keyboard 42, or the like). When the 3D stereoscopic image is rotated, as shown in FIG. 3, it is preferable that the coordinate axes are displayed on each side of the 3D configuration (cube in the figure) that forms the coordinate space 6. The 3D configuration of the coordinate space 6 becomes clear because of these coordinate axes, so a change of the direction of the 3D distribution chart at the time when the 3D stereoscopic image is rotated is easily recognized.

The 3D stereoscopic image displayed on the display 43 may be rotated optionally by an input from a user or may be always rotated slowly in a certain direction or in an uncertain direction. By displaying the 3D stereoscopic image as a moving image that is always rotated, the stereoscopic effect can be increased as compared to the display with a still image.

Figure 9:
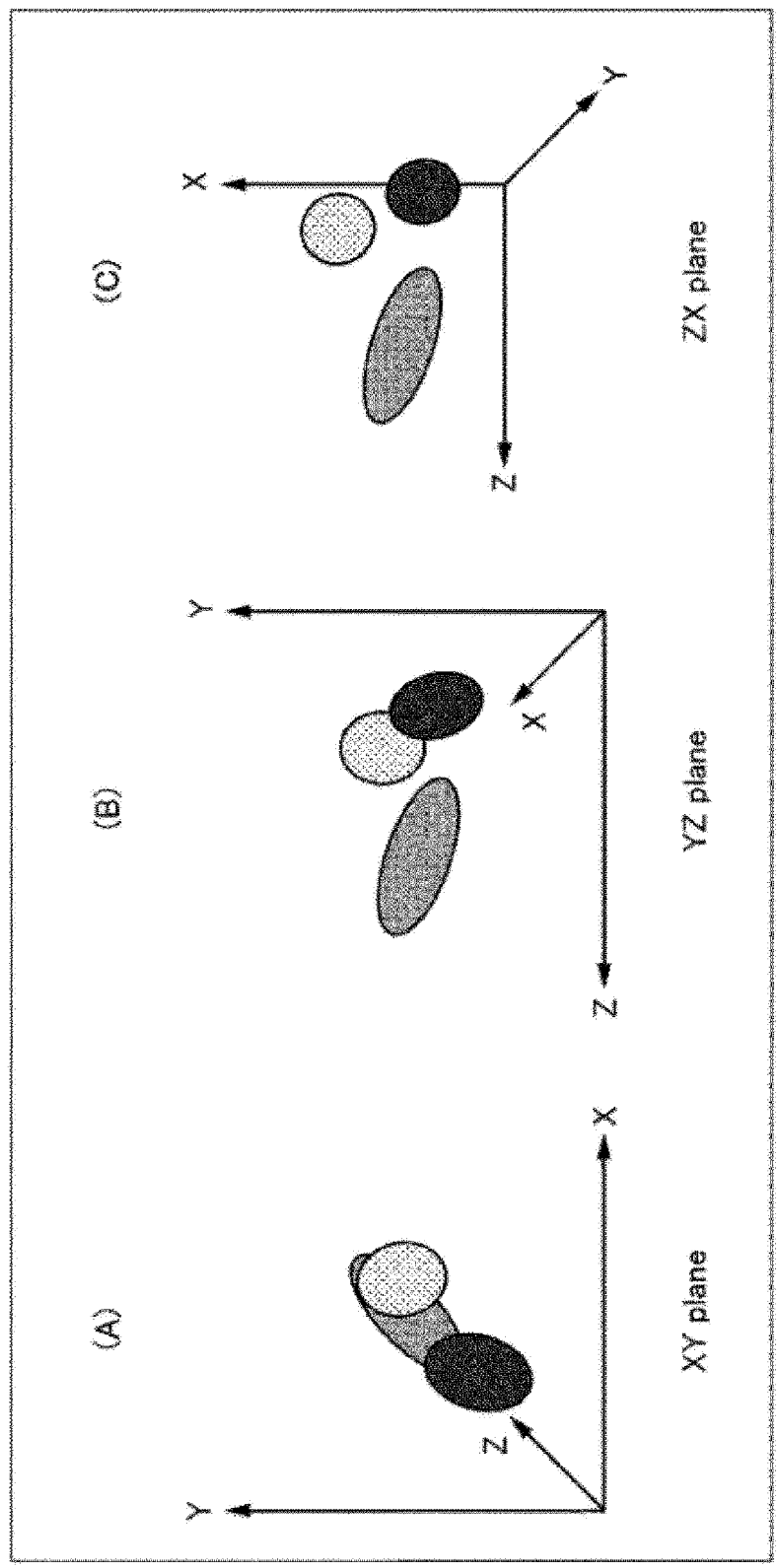
FIG. 9 is a conceptual diagram for explaining the stereoscopic observation images in the 3D distribution charts from the respective coordinate axes.

Further, the 3D stereoscopic image displayed on the display 43 is automatically rotated up to a direction such that the stereoscopic observation image from a coordinate axis direction selected by a user is provided on the basis of an input signal of the user at any timing during a rotation operation by the user or an automatic rotation. In FIG. 9, the stereoscopic observation images of the 3D distribution charts from the respective coordinate axes are shown. (A), (B), and (C) of FIG. 9 indicate observation images from a Z-axis direction, an X-axis direction, and a Y-axis direction, respectively. The switching of the viewpoint from the respective coordinate axes may be set so that the image is rotated at a viewpoint in the Z-axis direction by an input of Z key with the keyboard 42, and the image is rotated at a viewpoint from the Z-axis direction to the X-axis direction by an input of X key, for example. Further, the switching of the viewpoint from the respective coordinate axes may be performed by clicking an icon displayed on the display 43 with the mouse 41, for example. In this way, with the simple inputs, the viewpoint from the coordinate axes is switched, thereby making it possible to observe the 3D stereoscopic image, with the result that the user easily grasps the characteristic distribution of the microparticles in the 3D distribution chart.

It should be noted that in the case where the 3D stereoscopic image is always rotated and displayed on the display 43, it is preferable that the 3D stereoscopic image be rotated so as to maintain a vertical direction of the 3D distribution chart. That is, it is preferable that the 3D stereoscopic image is rotated with any one selected from among an XY plane, a YZ plane, and a ZX plane of the 3D distribution chart is always directed downwards in the distribution chart. Specifically, for example, in the case where the 3D stereoscopic image shown in (A) of FIG. 9 is always rotated, the image is rotated so that the ZX plane is always disposed on the bottom surface of the 3D distribution chart. At this time, the image may be rotated while tilting the rotation axis of the 3D distribution chart or changing a tilted angle thereof. In this way, by imposing a certain restriction on the rotation direction of the 3D stereoscopic image, the user more easily perceives a viewpoint direction of the user with respect to the 3D distribution chart, with the result that it is possible to prevents the case where the user cannot grasp the direction of the 3D distribution chart.

Figure 10:
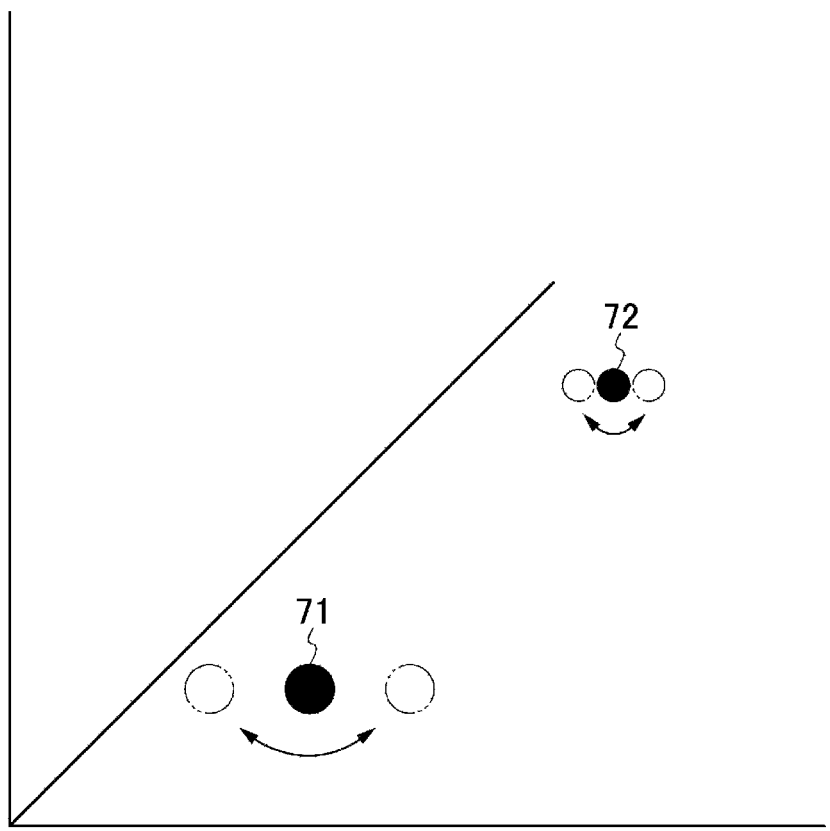
FIG. 10 is a conceptual diagram for explaining a stereoscopic observation image of a moving image obtained by swinging a graphic corresponding to the microparticle.

The 3D stereoscopic image displayed on the display 43 may be displayed with such a moving image that the graphics corresponding to the microparticles are swung. At this time, as compared to graphics observed backward when the stereoscopic viewing is performed, graphics observed forward are swung more intensely. A conceptual diagram of the stereoscopic images of the graphics to which the swinging operation is given is shown in FIG. 10. The graphics 71 and 72 are swung rightward and leftward as indicated by the arrows in the figure, and a rightward and leftward swinging range is larger for the graphic 71 observed forward and smaller for the graphic 72 observed backward. In this way, as compared to the graphic observed backward when the stereoscopic viewing is performed, the graphic observed forward is displayed in the more intensely swinging manner, with the result that the depth is given to the stereoscopic image of the 3D stereoscopic image, and the stereoscopic effect can be increased.

Further, in the case where the 3D stereoscopic image is displayed with a moving image, the graphics corresponding to the microparticles may be displayed in a blinked manner. At this time, by displaying the graphics observed forward at the time of the stereoscopic viewing in a more frequently blinked manner than the graphics observed backward, it is possible to further increase the stereoscopic effect of the 3D stereoscopic image.

Furthermore, in the case where the measurement data 32 includes measurement values at the plurality of time points, it is possible to display the 3D stereoscopic image of the 3D distribution chart at the time points with a moving image. As a result, in the example in which the association or dissociation of the cell-surface molecular complexes is measured as described above, it is possible to confirm a change with time in the association or the like of the cell-surface molecular complexes on the moving image.

As described above, the 3D data analysis apparatus according to the present invention is devised to increase the stereoscopic effect of the 3D stereoscopic image displayed. Therefore, even in the case of the 3D distribution chart constituted of only points (graphics corresponding to the microparticles) and lines (coordinate axes), it is possible for a user to analyze the measurement data while preferably visually confirming the stereoscopic image and easily and instinctively specify the microparticles and the microparticle small population to be analyzed on the distribution chart.

4. 3D Data Analysis Program

A 3D data analysis program according to the present invention causes a computer to execute a step of calculating the positions and the graphics in the coordinate space with the three kinds of variables selected from the measurement data of the microparticles being the coordinate axes and creating the 3D stereoscopic image that represents the characteristic distribution of the microparticles and a step of displaying the 3D stereoscopic image.

A description will be given on the basis of the above embodiment with reference to FIGS. 1 and 2 again. The 3D data analysis program is stored and held in the hard disk 30 (see, reference numeral 31 in the figure). The 3D data analysis program is read in the memory 20 under the control of the operating system (OS) 33 and executes a creation process of the 3D stereoscopic image of the 3D distribution chart in the data processing unit 120 and a display process of the 3D stereoscopic image on the display unit 142.

The 3D data analysis program can be recorded in a computer-readable recording medium. As long as the recording medium is computer-readable, the recording medium is not particularly limited. For example, a disk-type recording medium such as a flexible disk and a CD-ROM is used. Further, a tape type recording medium such as a magnetic tape may be used.

INDUSTRIAL APPLICABILITY

By the 3D data analysis apparatus according to the present invention, it is possible to easily and instinctively specifying the microparticles and the microparticle small populations to be analyzed without referring to a lot of histograms or cytograms or imaging the 3D distribution chart. Therefore, the 3D data analysis apparatus according to the present invention is used along with a flow cytometer, for example, and is usable to easily analyze characteristics of cells or microbes with high accuracy in the fields of medicine, public health, drug discovery, and the like.

It should be understood that various changes and modifications to the presently preferred embodiments described herein will be apparent to those skilled in the art. Such changes and modifications can be made without departing from the spirit and scope of the present subject matter and The invention is claimed as follows:

1. An information processing apparatus, comprising:
   a data storage configured to store measurement data of microparticles;
   a data processor configured to create a 3D image in a coordinate space with three types of variables from the measurement data, the 3D image represents a characteristic distribution of the microparticles; and
   a display configured to display a 3D stereoscopic image based on the 3D image,
   wherein a gating region is configured to be set by an input in the 3D stereoscopic image, the gating region is a 3D space displayed in the 3D stereoscopic image,
   wherein the 3D stereoscopic image is configured to be rotated or scaled up or down along with the gating region by the input, and
   wherein the 3D stereoscopic image is configured to be displayed as a moving image, and wherein a graphic observed in a forward orientation in the 3D stereoscopic image is configured to swing more broadly than a graphic observed in a backward orientation.

2. The information processing apparatus according to claim 1, wherein the three types of variables are selected from the group consisting of forward scattered light of the microparticles, side scatter of the microparticles, fluorescent light of the microparticles and impedance of the microparticles.

3. The information processing apparatus according to claim 1, wherein the input is configured to select the three types of variables.

4. The information processing apparatus according to claim 1, wherein the 3D stereoscopic image includes graphics corresponding to the microparticles in the coordinate space, and wherein the graphics are polyhedrons each including polygons.

5. The information processing apparatus according to claim 1, wherein the 3D stereoscopic image includes graphics corresponding to the microparticles in the coordinate space, and wherein the graphics observed forward are displayed to be darker than the graphics observed backward.

6. The information processing apparatus according to claim 1, wherein the 3D image is formed in coordinate axes corresponding to the three types of variables, and wherein the coordinate axes are displayed on respective sides of a coordinate space.

7. The information processing apparatus according to claim 1, wherein the 3D image is formed in coordinate axes corresponding to the three types of variables, and wherein a part of the coordinate axes observed forward is displayed to be thicker than a part thereof observed backward.

8. The information processing apparatus according to claim 1, wherein the 3D image is formed in coordinate axes corresponding to the three types of variables, and wherein at least one of the coordinate axes is a biexponential axis.

9. The information processing apparatus according to claim 1, further comprising glasses for viewing the 3D stereoscopic image.

10. A microparticle analysis system comprising the information processing apparatus according to claim 1 and a microparticle measurement apparatus.

11. An information processing method comprising:
    creating a 3D image in a coordinate space with three types of variables from measurement data of microparticles, the 3D image represents a characteristic distribution of the microparticles; and
    displaying a 3D stereoscopic image based on the 3D image on a display,
    wherein a gating region is configured to be set in the 3D stereoscopic image, the gating region is a 3D space displayed in the 3D stereoscopic image,
    wherein the 3D stereoscopic image is configured to be rotated or scaled up or down along with the gating region, and
    wherein the 3D stereoscopic image is configured to be displayed as a moving image, and wherein a graphic observed in a forward orientation in the 3D stereoscopic image is configured to swing more broadly than a graphic observed in a backward orientation.

12. The information processing method according to claim 11, wherein the three types of variables are selected from the group consisting of forward scattered light of the microparticles, side scatter of the microparticles, fluorescent light of the microparticles and impedance of the microparticles.

13. The information processing method according to claim 11, further comprising: selecting the three types of variables.

14. The information processing method according to claim 11, further comprising viewing the 3D stereoscopic image through glasses.

15. A non-transitory machine-readable medium having an information processing program stored thereon that is configured to cause a computer to execute at least the steps of:
    creating a 3D image in a coordinate space with three types of variables from measurement data of microparticles, the 3D image represents a characteristic distribution of the microparticles; and
    displaying a 3D stereoscopic image based on the 3D image on a display,
    wherein a gating region is configured to be set in the 3D stereoscopic image, the gating region is a 3D space displayed in the 3D stereoscopic image,
    wherein the 3D stereoscopic image is configured to be rotated or scaled up or down along with the gating region, and
    wherein the 3D stereoscopic image is configured to be displayed as a moving image, and wherein a graphic observed in a forward orientation in the 3D stereoscopic image is configured to swing more broadly than a graphic observed in a backward orientation.

16. The non-transitory machine-readable medium according to claim 15, wherein the three types of variables are selected from the group consisting of forward scattered light of the microparticles, side scatter of the microparticles, fluorescent light of the microparticles and impedance of the microparticles.

17. The non-transitory machine-readable medium according to claim 15, further comprising: selecting the three types of variables.

* * * * *